United States Patent [19]

Pomidor

[11] Patent Number: 4,831,179
[45] Date of Patent: May 16, 1989

[54] ARYLMETHYLENESUL-FONAMIDOACETONITRILE DERIVATIVES

[75] Inventor: Patricia B. Pomidor, Fremont, Calif.

[73] Assignee: Chevron Research Company, San Francisco, Calif.

[21] Appl. No.: 930,837

[22] Filed: Nov. 14, 1986

Related U.S. Application Data

[63] Continuation-in-part of Ser. No. 720,233, Apr. 5, 1985, abandoned.

[51] Int. Cl.$^4$ ............................................. C07C 121/52
[52] U.S. Cl. .................................... 558/390; 71/103
[58] Field of Search .......................................... 558/390

[56] References Cited

U.S. PATENT DOCUMENTS

| | | | |
|---|---|---|---|
| 4,113,463 | 9/1978 | Oshio et al. | 260/465 E X |
| 4,169,719 | 10/1979 | Levitt | 71/92 |
| 4,191,553 | 3/1980 | Reap | 71/92 |
| 4,468,425 | 8/1984 | Takematsu et al. | 71/88 |
| 4,481,029 | 11/1984 | Levitt | 71/93 |
| 4,487,626 | 12/1984 | Zimmerman | 71/90 |
| 4,491,467 | 1/1985 | Peterson | 71/93 |
| 4,495,365 | 1/1985 | Pallos | 564/91 |
| 4,501,607 | 2/1985 | Levitt | 71/93 |

FOREIGN PATENT DOCUMENTS

| | | |
|---|---|---|
| 2022694 | 11/1970 | Fed. Rep. of Germany . |
| 2431734 | 1/1976 | Fed. Rep. of Germany . |
| 2126586 | 3/1984 | United Kingdom . |

*Primary Examiner*—Anton H. Sutto
*Attorney, Agent, or Firm*—S. R. La Paglia; R. C. Gaffney; L. S. Squires

[57] ABSTRACT

Arylmethylenesulfonamidoacetonitrile derivatives. The compounds are useful as selective hericides especially with respect to the prevention and elimination of barnyardgrass in grass crops, especially rice.

35 Claims, No Drawings

ARYLMETHYLENESULFONAMIDOACETONITRILE DERIVATIVES

CROSS REFERENCE TO RELATED APPLICATIONS

This application is a continuation-in-part of co-pending U.S. Application Ser. No. 720,233, filed Apr. 5, 1985, now abandoned, the entire disclosure of which is hereby incorporated by reference.

BACKGROUND OF THE INVENTION

This invention relates to arylmethylenesulfonamidoacetonitrile derivatives and to the use of such compounds as herbicides and plant growth regulators. In a further aspect the invention relates to intermediate and processes for preparing such compounds.

Where herbicides are used to eliminate weeds from crops the herbicide must be effective against the target weed at the application rate used yet safe with respect to the crop. In the case where both the crop and weed species are grasses, it is very difficult to chemically eliminate the grassy weeds without injuring the crop. This is particularly the situation in the case of barnyardgrasses in rice crops.

U.S. Pat. No. 4,191,553 discloses certain arylsulfonamidoamidoheterocycle (Col. 1, lines 29–46) and aryloxysulfonamidocarboxamidoheterocycle herbicides. U.S. Pat. No. 4,169,719 discloses arylsulfonamidocarboxamidoheterocycle herbicides. U.S. Pat. No. 4,468,245 discloses N-(2,3-epoxypropylene)-N-araalkyl sulfonamide herbicides reported to have less phytotoxicity against rice.

W. German Patent Application DE No. 2,431,734 discloses benzylsulfonamidoacetic acid; benzylbenzylsulfonamidoacetamide; and ethyl (N-methyl-benzylsulfonamido)acetate as intermediate for immunosuppressant. W. German Patent Application DE No. 2,022,694 discloses N,N-dimethyl-(2-carboxybenzylsulfonamido)acetamide and 2-cyanobenzylsulfonamido)acetamide as intermediates for antispasmodics and narcotics to photosensitive protecting groups. British Pat. No. 2,126,586 discloses certain herbicidal sulfonylureas as giving complete kill of barnyardgrass without damage to rice.

SUMMARY OF THE INVENTION

The present invention provides compounds having excellent selective pre-emergence and post-emergence herbicidal activity against barnyardgrass. In addition, the present compounds exhibit excellent safety with respect to both broadleaf and grassy crops, including rice.

The compounds of the present invention can be represented by the following formula:

(I)

wherein R is hydrogen, lower alkyl having 1 through 6, preferably 1 through 4, carbon atoms; cycloalkyl having 3 through 6 carbon atoms; cycloalkylalkyl having 3 through 6 carbon atoms in the cycloalkyl moiety and 1 or 2 carbon atoms in the alkyl moiety; lower alkenyl having 2 through 6, preferably 2 through 4, carbon atoms; lower alkynyl having 2 through 6 carbon atoms; 3-iodopropargyl; alkoxyalkyl wherein the alkoxy and alkyl moieties independently have 1 through 6, preferably 1 through 4 carbon atoms; alkylthioalkyl wherein the alkyl moieties independently have 1 through 6, preferably 1 through 4, carbon atoms; epoxyalkylmethyl having the formula R'—CH$_2$— wherein R' is epoxyalkyl having 1 through 5 carbon atoms; cyanomethyl; or haloalkylmethyl having 2 through 4 carbon atoms and 1 through 4 halo atoms independently selected from the group of fluoro chloro and bromo; and Ar is a substituted phenyl selected from the group of tetrafluorophenyl; pentafluorophenyl; trisubstituted phenyls having three substituents independently selected from the group of fluoro, chloro, bromo or trifluoromethyl; or a substituted phenyl having the formula

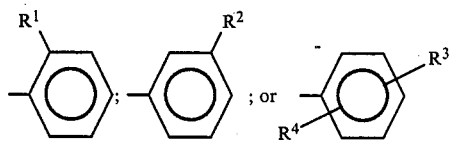

wherein $R^1$ is methyl, trifluoromethyl or chloro; $R^2$ is halo, alkyl having 1 through 4 carbon atoms, alkoxy having 1 through 4 carbon atoms, fluoroalkyl having 1 through 4 fluoro atoms and 1 through 4 carbon atoms (preferably trifluoromethyl) or nitro; one of $R^3$ or $R^4$ is trifluoromethyl or chloro and the other is halo, alkyl having 1 through 4 carbon atoms, alkoxy having 1 through 4 carbon atoms, or fluoroalkyl having 1 through 4 fluoro atoms and 1 through 4 carbon atoms, or nitro.

In the case where the R substituent creates an asymmetric carbon atom the compounds can also exist as optical isomers. Also depending on the particular substituent, in some instances the compounds also exist as geometric isomers. The above formula is intended to encompass the respective individual isomers as well as mixtures thereof and the respective isomers as well as mixtures thereof are encompassed within the invention.

The compounds of Formula (I) wherein R is hydrogen are only weakly active or wholly inactive as herbicides but, are useful as intermediates to prepare various R substituted analogs which exhibit excellent selective herbicidal activity against barnyardgrass.

In a further aspect the invention provides a herbicidal composition comprising a compatible carrier and a herbicidally effective amount of the compound(s) of the invention or mixtures thereof.

The present invention also provides a method for preventing or controlling the growth of unwanted vegetation, which comprises treating the growth medium and/or the foliage of such vegetation with a herbicidally effective amount of the compound(s) of the invention or mixtures thereof.

In another aspect, the present invention provides a plant growth regulating composition comprising a compatible carrier and a plant growth regulating amount of the compound(s) of the invention or mixtures thereof, effective to alter the normal growth pattern of said plants.

The present invention also provides a method for regulating plant growth which comprises treating the growth medium and/or the foliage of such vegetation with a plant growth regulating effective amount of the compound(s) of the invention or mixtures thereof, effective to alter the normal growth pattern of said plants.

The present invention also provides chemical intermediates and processes for preparing the herbicidal compounds of the invention.

The invention will be further described hereinbelow.

FURTHER DESCRIPTION OF THE INVENTION AND THE PREFERRED EMBODIMENTS

Illustrations of typical compounds of Formula (I) of the present invention can be had by reference to Examples 1-5 set forth hereinbelow on pages 17 to 30.

In terms of substituents and herbicidal activity, the preferred compounds are those wherein R is lower alkyl having 1 through 4 carbon atoms, lower alkenyl, lower alkynyl, fluoroalkylmethyl, cycloalkyl, and methoxymethyl, especially preferred R-groups are methyl, ethyl, 2-propynyl, 2-fluoroethyl, 2,2,2-trifluoroethyl, cyclopropyl and methoxymethyl. $R^1$ is H; Ar is pentafluorophenyl, monosubstituted phenyl more preferably having its single substituent at the 3-position. Especially preferred Ar-groups are the groups 3-trifluoromethylphenyl, and 3-chlorophenyl. In the case of disubstituted Ar groups, the Ar groups 3,5-dichlorophenyl, 2-chloro-5-trifluoromethylphenyl and 3,5-ditrifluoromethylphenyl are preferred. In the case of trisubstituted Ar groups, the Ar groups, 2,3-dichloro-5-trifluoromethylphenyl and (2,3,6-trichlorophenyl) are preferred. Also, both the mono- and disubstituted Ar-groups are generally preferred to the trisubstituted Ar-group.

Most preferably the compounds contain a combination of a preferred Ar and a preferred R substituent.

Examples of specific compounds which exhibit excellent selective herbicidal activity against barnyardgrass, include:

(N-ethyl-3-trifluoromethylbenzylsulfonamido)acetonitrile;
(N-allyl-3-trifluoromethylbenzylsulfonamido)acetonitrile;
(N-2'-propynyl-3-trifluoromethylbenzylsulfonamido)acetonitrile;
(N-2'-fluoroethyl-3-trifluoromethylbenzylsulfonamido)acetonitrile;
(N-2',2',2'-trifluoroethyl-3-trifluoromethylbenzylsulfonamido)acetonitrile;
(N-cyclopropyl-3-trifluoromethylbenzylsulfonamido)acetonitrile;
(N-methyoxymethyl-3-trifluoromethylbenzylsulfonamido)acetonitrile;
(N-ethyl-3-chlorobenzylsulfonamido)acetonitrile;
(N-ethyl-3,5-dichlorobenzylsulfonamido)acetonitrile;
(N-ethyl-2-chloro-5-trifluoromethylbenzylsulfonamido)acetonitrile;
(N-ethyl-pentafluorophenylmethylsulfonamido)acetonitrile;
(N-ethyl-3,5-di-trifluoromethylbenzylsulfonamido)acetonitrile; and
(N-ethyl-2,3-dichloro-5-trifluoromethylbenzylsulfonamido)acetonitrile.

The compounds of Formula (I) can be prepared by the following schematically represented process:

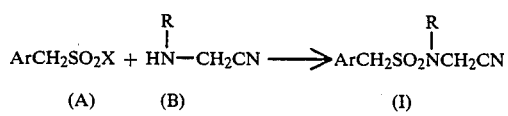

wherein X is chloro or bromo, preferably chloro, and Ar and R are as defined herein above.

This process can be conveniently effected by contacting Compound (A) with Compound (B) or an addition salt thereof, preferably in the presence of a base, and generally water, preferably in an inert organic solvent.

Typically, this process is conducted at temperatures in the range of about from 0° to 100° C., preferably about from 20° to 80° C., for about from 2 to 8 hours, preferably about from 3 to 5 hours, using about from 1 to 5, preferably 1.5 to 3 moles of Compound (B) per mole of Compound (A). Suitable bases which can be used include, for example, inorganic bases such as for example, potassium carbonate, sodium hydroxide, sodium carbonate, and the like, as well as organic bases such as for example trialkylamine (for example triethylamine) pyridine, and the like. Where an inorganic base is used the process is also conducted in the presence of water and higher reaction temperatures are required. The base serves to scavenge the hydrogen halide formed by the reaction and also when a salt of Compound (B) is used the base serves to liberate Compound (B) for the reaction. Suitable organic solvents which can be used include, for example, methylene chloride, 1,2-dichloroethane, and the like, and compatible mixtures thereof.

Best results are typically obtained using about one and a half equivalents of Compound (B) and about one equivalent of base (e.g., pyridine) per equivalent of Compound (A) and running the reaction in dichloromethane.

The starting materials of Formula (A) and (B) are known compounds or can be prepared by the adaptation of known procedures using appropriately substituted starting materials. The arylmethylsulfonyl chlorides of Formula (A) can, for example, be prepared by the following schematically represented process:

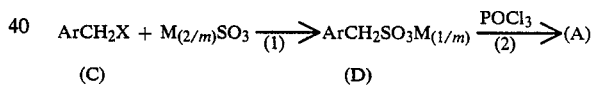

wherein X is chloro or bromo; M is a cation and m is its valence; and R is as defined hereinabove.

The first step of this process can be conveniently effected by contacting Compound (C) with a sulfite salt, in water and optionally an inert organic solvent.

Typically, this process is conducted at temperatures in the range of about from 70° to 100° C., preferably 90° to 100° C., for about from 2 to 8 hours, preferably 4 to 5 hours, using about from 1 to 2, preferably 1 to 1.2 mole equivalents of sulfite salt per mole of Compound (C).

Suitable sulfite salts (C) which can be used include, for example, alkali metal sulfites, for example, potassium sulfite; sodium sulfite; ammonium sulfite; and the like. Typically, simple sulfites, such as sodium sulfite, are preferred as they are relatively inexpensive and give good results.

Suitable optional inert organic solvents which can be used include, for example, liquid alkanols, glycols, dimethylformamide and the like, and compatible mixtures thereof.

The starting materials of Formula (C) are generally known materials and can be prepared by known procedures, or obvious modifications thereof (i.e., substitution of appropriate starting materials). For example, many of the starting materials of Formula (C) can be prepared by halogenating the corresponding substituted toluenes by adapting the procedure described in Organic Synthesis, Collective Vol. V, page 825. Compounds such as m-trifluoromethylbenzyl chloride can be conveniently prepared via chloromethylation of the corresponding toluene derivative; e.g. α, α, α-trifluorotoluene.

The second step of this process can be conveniently effected by contacting Compound (D) with phosphorous oxychloride optionally in a solvent.

Typically, this process is conducted at temperatures in the range of about from 80° to 200° C., preferably 100° to 110° C. for about from 2 to 8 hours, preferably 4 to 5 hours, using about from 1 to 10, preferably 1.5 to 5 moles of phosphorous oxychloride per mole equivalent of Compound (D). If desired, excess phosphorous oxychloride can be used as solvent or inert organic solvents such as toluene could also be used.

The compounds of Formula (A) having an ortho or an ortho and para alkyl substituent are typically more conveniently prepared by chlorination of the corresponding alkylbenzylmercaptan by adapting the procedure described in *J. Am. Chem. Soc.*, V. 60, p. 1486 (1938).

In some instances it is preferable to prepare certain of the R-substituted compounds of Formula (I) from the corresponding R-unsubstituted compound of Formula (I). This process can be schematically represented by the overall reaction equation:

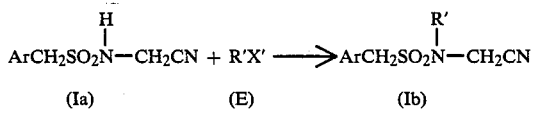

(Ia)    (E)    (Ib)

wherein Ar is as defined hereinabove and R' is as defined for R, hereinabove, but is other than hydrogen; and X' is bromo or iodo, or R'X' can be dialkylsulfate.

The above process is a general procedure but is especially useful to prepare the compounds of Formula (I) wherein R is alkyl, alkenyl, alkoxyalkyl, epoxyalkylmethylene, haloalkylmethyl, haloalkylmethylene, cyanomethyl or alkylthioalkyl. (The analogs wherein R' is hydroxyalkyl can also be prepared via this method. The hydroxyalkyl compounds can in turn be used to prepare the corresponding R as haloalkylmethyl compounds of Formula (I) via halide replacement.) This process can be effected as a phase transfer reaction by contacting Compound (Ia) with Compound (E) in water and an inert water immiscible organic solvent in the presence of base and a phase transfer agent.

This process is typically conducted at temperatures in the range of about from 0° to 80° C., preferably, 25° to 80° C., for about from 1 to 36 hours, preferably 2 to 24 hours using about from 1 to 2 moles, preferably 1 to 1.2 mole equivalents of Compound (E) and 1 to 2 mole equivalents, preferably about 1 mole equivalent of base and 0.05 to 1 mole equivalents, preferably 0.05 to 0.3 mole equivalents of phase transfer agent per mole of Compound (Ia).

Suitable inert water immiscible organic solvents which can be used include, for example, chloroalkanes, e.g., methylene chloride, 1,2-dichloroethane, and trichloroethane; toluene, and the like and compatible mixtures thereof. Typically about from 1 to 8, preferably 3.5 to 5.5 liters of inert organic solvent are used per mole of Compound (Ia). Generally, water to immiscible solvent volume ratios of about from 1:3 to 1:20, preferably about 1:10 are used.

Suitable phase transfer agents which can be used are compounds which transfer hydrophilic ions into liquid lipophilic organic mediums and include benzyl triethylammonium chloride, methyl trioctylammonium chloride, tetrabutyl ammonium chloride, tetrabutyl ammonium bromide and the like. Very good results are typically obtained using benzyl triethylammonium chloride as the phase transfer agent.

Suitable bases which can be used include, for example, sodium hydroxide, potassium hydroxide, sodium carbonate, potassium carbonate, lithium carbonate, and the like.

The above process can also be conducted by contacting Compound (Ia) with Compound (E) in the presence of a strong base, such as sodium hydride, preferably in an inert organic solvent.

This process is typically conducted at temperatures in the range of about from 0° to 100° C., preferably, 25° to 60° C., for about from 1 to 24 hours, preferably 2 to 4 hours using about from 1 to 2 moles, preferably 1 to 1.1 mole equivalents of the Compound (E) and 1 to 1.2 moles, preferably about 1 to 1.1 mole equivalents of strong base per mole of Compound (Ia).

Suitable strong bases which can be used include, for example, sodium hydride, lithium hydride, potassium hydride, and the like. Suitable inert organic solvents which can be used include for example dimethylformamide, tetrahydrofuran, dimethylsulfoxide, and the like and compatible mixtures thereof.

The compounds of Formula (I) can also be prepared from the corresponding arylmethylenesulfonamide derivatives by the following schematically represented process:

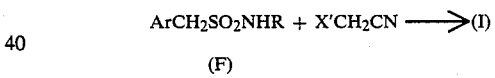

(F)

wherein Ar and R are as defined hereinabove and X' is bromo or iodo.

This process is a convenient synthesis for the R is cyclopropyl compounds.

This process can be conducted as a phase transfer reaction and can be effected by contacting Compound (F) with bromo- or iodoacetonitrile in water and an inert water immiscible organic solvent in the presence of base and a phase transfer agent.

This process is typically conducted at temperatures in the range of about from 0° to 80° C., preferably, 25° to 80° C., for about from 1 to 36 hours, preferably 2 to 24 hours using about from 1 to 2 moles, preferably 1 to 1.2 moles of bromo- or iodoacetonitrile and about 1 to 2 mole equivalents, preferably about 1 to 1.2 mole equivalents of weak base and 0.05 to 1 mole equivalents, preferably 0.05 to 0.3 mole equivalents of phase transfer agent per mole of Compound (F).

Suitable immiscible solvents, bases, and phase transfer agents include those illustrated with respect to the previously described phase transfer reaction.

This process can also be effected by contacting Compound (F) with bromo- or iodoacetonitrile in the presence of base, preferably in an inert organic solvent.

This process is typically conducted at temperatures in the range of about from 0° to 100° C., preferably, 25° to 60° C., for about from 1 to 24 hours, preferably 2 to 4 hours using about from 1 to 2 moles, preferably 1 to 1.1 moles of bromo- or iodoacetonitrile and 1 to 1.2 mole equivalents, preferably about 1.1 mole equivalents of strong base per mole of Compound (Ia).

Suitable strong bases which can be used include, for example, lithium hydride, sodium hydride, potassium hydride, and the like. Suitable inert organic solvents which can be used include for example, dimethylformamide, tetrahydrofuran, dimethylsulfoxide, and the like and compatible mixtures thereof.

The starting materials of Formula (F) can be prepared by reacting the corresponding compound of Formula (A), with ammonium hydroxide (R=H) or the corresponding R primary amine ($RNH_2$).

GENERAL PROCESS CONDITIONS

In the above-described processes, it is generally preferable to separate the respective products before proceeding with the next step in the reaction sequence, except where described as an in situ step or unless otherwise expressly stated. These products can be recovered from their respective reaction product mixtures by any suitable separation and purification procedure, such as, for example, recrystallization and chromatography. Suitable separation and purification procedures are, for example, illustrated in the Examples set forth hereinbelow.

Generally, the reactions described above are conducted as liquid phase reaction and hence pressure is generally not significant except as it affects temperature (boiling point) where reactions are conducted at reflux. Therefore, these reactions are generally conducted at pressures of about from 300 to 3,000 mm of mercury and conveniently conducted at about atmospheric or ambient pressure.

It should also be appreciated that where typical or preferred process conditions (e.g., reaction temperatures, times, mole ratios of reactants, solvents, etc.) have been given, that other process conditions could also be used. Optimum reaction conditions (e.g., temperature, reaction time, mol ratios, solvents, etc.) may vary with the particular reagents or organic solvents used but can be determined by routine optimization procedures.

Where optical isomer mixtures are obtained, the respective optical isomers can be obtained by conventional resolution procedures. Geometric isomers can be separated by conventional separation procedures which depend upon differences in physical properties between the geometric isomers.

DEFINITIONS

As used herein the following terms have the following meanings unless expressly stated to the contrary:

The term "lower alkyl" refers to both straight-and branched-chain alkyl groups having a total of from 1 through 6 carbon atoms, preferably 1 through 4 carbon atoms and includes primary, secondary and tertiary alkyl groups. Typical lower alkyls include, for example, methyl, ethyl, n-propyl, isopropyl, n-butyl, t-butyl.

The term "lower alkylene" refers to both straight chain and branch chained alkylene groups having 1 through 6 carbon atoms, preferably 1 through 4 carbon atoms and includes, for example,

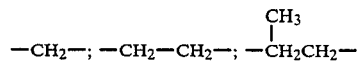

and the like.

The term "lower alkenyl" refers to alkenyl groups having 2 through 6, preferably 2 through 4, carbon atoms and includes, for example, vinyl, 1-propenyl, 2-propenyl, 1-methylvinyl, 1-butenyl, 2-methylprop-1-enyl and the like.

The term "lower alkoxy" refers to the group —OR' wherein R' is lower alkyl.

The term "lower alkylthio" refers to the group —SR' wherein R' is lower alkyl.

The term "lower alkoxyalkyl" refers to the group R'OR"— wherein R' and R" are independently straight chain or branched chain alkyl groups having 1 through 3 carbon atoms.

The term "cycloalkylalkyl" refers to the group $R^aR^b$— wherein $R^a$ is cyclopropyl having 3 through 6 carbon atoms and $R^b$ is methyl or ethyl.

The term "lower alkylthioalkyl" refers to the group R'SR"— wherein R' and R" are independently straight chain or branched chain alkyl groups having 1 through 3 carbon atoms.

The term "haloalkylmethyl" or (haloalkyl) methyl refers to the group having the formula R'''$CH_2$— wherein R''' is a branched or straight chain haloalkyl. The term haloalkylmethyl includes, for example, 2,2-dichloroethyl; 2-chloropropyl; and the like.

The term "halo" refers to the group of fluoro, chloro, bromo and iodo.

The term (N-methyl-3-trifluoromethylbenzylsulfonamido)acetonitrile refers to the compound having the structural formula

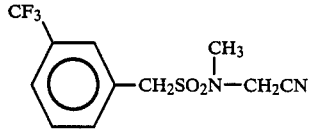

The term "room temperature" or "ambient temperature" refers to about 20°-25° C.

UTILITY

The herbicidal compounds of the invention exhibit excellent selective pre- and post-emergence phytotoxicity against barnyardgrass (*Echinochloa crusgalli*) also known as watergrass, and have excellent crop safety. The compounds are especially useful for the elimination and prevention of barnyardgrass in rice crops.

Generally, for post-emergent applications, the herbicidal compounds are applied directly to the foliage or other plant parts. For pre-emergence applications, the herbicidal compounds are applied prospectively to the growth medium (habitat) for the plant. The optimum amount of the herbicidal compound or composition will vary with the particular plant species, and the extent of plant growth, if any, and the particular part of the plant which is contacted and the extent of contact. The optimum dosage can also vary with the general location, or environment (e.g., sheltered areas such as greenhouses compared to exposed areas such as fields), and type and degree of control desired. Generally, for both pre- and post-emergent control, the present compounds are applied at rates of about from 0.02 to 60 kg/ha, preferably about from 0.02 to 10 kg/ha.

Also, although in theory the compounds can be applied undiluted, in actual practice they are generally applied as a composition or formulation comprising an effective amount of the compound(s) and an acceptable carrier. An acceptable or compatible carrier (agriculturally acceptable carrier) is one which does not significantly adversely affect the desired biological effect achieved by the active compounds, save to dilute it. Typically, the composition contains about from 0.05 to 95% by weight of the compound of Formula (I) or mixtures thereof. Concentrates can also be made having high concentrations designed for dilution prior to application. The carrier can be a solid, liquid, or aerosol. The actual compositions can take the form of granules, powders, dusts, solutions, emulsions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seek hulls, wheat flour, wood flour, wood bark flour, and the like can also be used as carriers. Suitable liquid diluents which can be used include, for example, water, organic solvents (e.g., hydrocarbons such as benzene, toluene, dimethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils, and in the case of compositions designed for pre-emergence application agents which reduce the leachability of the compound or otherwise enhance soil stability.

The composition can also contain various compatible adjuvants, stabilizers, conditioners, insecticides, fungicides, and if desired, other herbicidally active compounds.

At reduced dosages the compounds of the present invention can be expected to exhibit plant growth regulating activity and can be used to alter the normal growth pattern of plants. For example, a number of the compounds show significant capacity to retard root growth.

As in the case of herbicides plant growth regulators can be applied in pure form, but more pragmatically, as in the case of herbicidal application, are applied in combination with a carrier. The same types of carriers as set forth hereinabove with respect to the herbicidal compositions can also be used. Depending on the desired application, the plant growth regulating composition can also contain, or be applied in combination with other compatible ingredients such as desiccants, defoliants, surface-active agents, adjuvants, fungicides, and insecticides. Typically, the plant growth regulating composition will contain a total of about from 0.005 to 90 wt. % of the compound(s) of Formula (I) depending on whether the composition is intended to be applied directly or diluted first.

A further understanding of the invention can be had in the following non-limiting Preparation(s) and Example(s). Wherein, unless expressly stated to the contrary, all temperatures and temperature ranges refer to the Centigrade system and the term "ambient" or "room temperature" refers to about 20° to 25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined at 60 mHz, signals are assigned as singlets (s), broad singlets (bs), doublets (d), double doublets (dd), triplets (t), double triplets (dt), quartets (q), and multiplets (m); and cps refers to cycles per second. Also where necessary examples are repeated to provide additional starting material for subsequent examples.

EXAMPLES AND PREPARATIONS

Preparation 1

3-Trifluoromethylbenzylsulfonyl Chloride (a) A mixture containing 50 g of 3-trifluoromethylbenzyl chloride and 32.4 g of sodium sulfite in 200 ml of water was refluxed for five hours and then concentrated by evaporation. The concentrate was then filtered to collect the precipitate (product). The precipitate was then washed with ethyl ethyl and then dried in a vacuum oven affording 61 g of sodium 3-trifluoromethylbenzylsulfonate.

(b) 10 g of sodium 3-trifluoromethylbenzylsulfonate was slowly added to 17.7 ml (29.1 g) of phosphorous oxychloride. The resulting slurry was stirred at 100° to 105° C. for five hours. The reaction mixture was then cooled and filtered. The filter cake was washed with methylene chloride, the washings were combined with the filtrate and then evaporated to dryness affording 8.9 g of 3-trifluoromethylbenzylsulfonyl chloride.

EXAMPLE 1

(N-Methyl-3-Trifluoromethylbenzylsulfonamido)Acetonitrile

In this example 36.1 g of 3-trifluoromethylbenzylsulfonyl chloride was added cautiously to a solution containing 29.8 g of the hydrochloride salt of methylaminoacetonitrile and 38.7 g of potassium carbonate in 130 ml of water at room temperature. The reaction mixture was maintained at about 70° C. for about four hours. The mixture was allowed to cool and then extracted with ethyl ether. The ethyl ether extract was dried over magnesium sulfate and evaporated to dryness. The residue was vacuum filtered through silica gel using 3% vol. tetrahydrofuran: chloroform as eluent. 29 g of the title compound was obtained as a waxy white solid.

Similarly by applying the general procedure described above using the appropriate starting materials the following compound can be prepared:
(N-methyl-3-1',2',2-trifluoroethylbenzylsulfonamido)acetonitrile;
(N-methyl-3-difluoromethylbenzylsulfonamido)acetonitrile;
(N-methyl-3-ethylbenzylsulfonamido)acetonitrile;
(N-methyl-3-t-butylbenzylsulfonamido)acetonitrile;
(N-methyl-3-nitrobenzylsulfonamido)acetonitrile;
(N-methyl-3-ethoxybenzylsulfonamido)acetonitrile;

(N-methyl-3-propoxycarbonylbenzylsulfonamido)acetonitrile;
(N-methyl-2-trifluoromethylbenzylsulfonamido)acetonitrile;
(N-methyl-2-3',4'-difluorobutylbenzylsulfonamido)acetonitrile;
(N-methyl-3-methoxybenzylsulfonamido)acetonitrile;
(N-methyl-3-fluorobenzylsulfonamido)acetonitrile;
(N-methyl-3-bromobenzylsulfonamido)acetonitrile;
(N-methyl-2-methylbenzylsulfonamido)acetonitrile;
(N-methyl-2-chlorobenzylsulfonamido)acetonitrile;
(N-methyl-2-bromo-5-trifluoromethylbenzylsulfonamido)acetonitrile;
(N-methyl-2-chloro-5-trifluoromethylbenzylsulfonamido)acetonitrile;
(N-methyl-3-chloro-5-difluoromethylbenzylsulfonamido)acetonitrile;
(N-methyl-3-chloro-4-methoxybenzylsulfonamido)acetonitrile;
(N-methyl-2-trifluoromethyl-6-methoxybenzylsulfonamido)acetonitrile;
(N-methyl-2-trifluoromethyl-3-ethylbenzylsulfonamido)acetonitrile;
(N-methyl-2-chloro-4-trifluoromethylbenzylsulfonamido)acetonitrile;
(N-methyl-2-fluoro-3-chlorobenzylsulfonamido)acetonitrile;
(N-methyl-3-chloro-5-iodobenzylsulfonamido)acetonitrile;
(N-methyl-2,4-di-trifluoromethylbenzylsulfonamido)acetonitrile;
(N-methyl-3,4,5-tri-trifluoromethylbenzylsulfonamido)acetonitrile;
(N-methyl-3,4-dichloro-5-fluorobenzylsulfonamido)acetonitrile;
(N-methyl-3-methylbenzylsulfonamido)acetonitrile;
(N-methyl-2-bromo-3-chloro-6-trifluoromethylthiobenzylsulfonamido)acetonitrile;
(N-methyl-2-chloro-3-fluoro-5-trifluoromethylbenzylsulfonamido)acetonitrile;
(N-methyl-2-bromo-4-fluoro-3-trifluoromethylbenzylsulfonamido)acetonitrile;
(N-methyl-2,3,6-trichlorobenzylsulfonamido)acetonitrile;
(N-cyanomethyl-3-trifluoromethylbenzylsulfonamido)acetonitrile;
(N-cyanomethyl-3-difluoromethylbenzylsulfonamido)acetonitrile;
(N-cyanomethyl-3-ethylbenzylsulfonamido)acetonitrile;
(N-cyanomethyl-3-t-butylbenzylsulfonamido)acetonitrile;
(N-cyanomethyl-3-3'4'-difluorobutylbenzylsulfonamido)acetonitrile;
(N-cyanomethyl-3-ethoxybenzylsulfonamido)acetonitrile;
(N-cyanomethyl-3-propoxybenzylsulfonamido)acetonitrile;
(N-cyanomethyl-2-1',2',2-trifluoroethylbenzylsulfonamido)acetonitrile;
(N-cyanomethyl-2-1',2'-difluoroethylbenzylsulfonamido)acetonitrile;
(N-cyanomethyl-3-methoxybenzylsulfonamido)acetonitrile;
(N-cyanomethyl-3-propylbenzylsulfonamido)acetonitrile;
(N-cyanomethyl-3-nitrobenzylsulfonamido)acetonitrile;
(N-cyanomethyl-2-chlorobenzylsulfonamido)acetonitrile;
(N-cyanomethyl-2-trifluoromethylbenzylsulfonamido)acetonitrile;
(N-cyanomethyl-2,5-di-trifluoromethylbenzylsulfonamido)acetonitrile;
(N-cyanomethyl-2-bromo-3-trifluoromethylbenzylsulfonamido)acetonitrile;
(N-cyanomethyl-3-methyl-5-trifluoromethylbenzylsulfonamido)acetonitrile;
(N-cyanomethyl-3-chloro-4-2',2'-difluoroethylbenzylsulfonamido)acetonitrile;
(N-cyanomethyl-2-chloro-6-ethylbenzylsulfonamido)acetonitrile;
(N-cyanomethyl-2-ethoxy-3-trifluoromethylbenzylsulfonamido)acetonitrile;
(N-cyanomethyl-2-chloro-3-trifluoromethylbenzylsulfonamido)acetonitrile;
(N-cyanomethyl-2-chloro-3-bromobenzylsulfonamido)acetonitrile;
(N-cyanomethyl-3-chloro-5-iodobenzylsulfonamido)acetonitrile;
(N-cyanomethyl-4-chloro-3-trifluoromethylbenzylsulfonamido)acetonitrile;
(N-cyanomethyl-2-chloro-4-2',3',3'-trifluoropropylbenzylsulfonamido)acetonitrile;
(N-cyanomethyl-2,4,5-trifluorobenzylsulfonamido)acetonitrile; and
(N-cyanomethyl-pentafluorophenylmethylsulfonamido)acetonitrile.

EXAMPLE 2

N-Ethyl-3-Trifluoromethylbenzylsulfonamidoacetonitrile

In this example 2 g of 3-trifluoromethylbenzylsulfonamidoacetonitrile was dissolved in 30 ml of dichloromethane. To this was added 0.32 g of sodium hydroxide dissolved in a minimum amount of water and 0.46 g of benzyltriethylammonium chloride. A solution of 1.1 ml of diethylsulfate in 5 ml of dichloromethane was added dropwise. The reaction mixture was stirred overnight at room temperature. Water was added to the reaction mixture, and the dichloromethane layer was separated. The water phase was extracted with dichloromethane. The organic phases were combined, dried over magnesium sulfate, filtered and stripped. Trituration of the solid yielded 1.4 g of the title compound as a white solid.

Similarly by adapting the general procedure used above using the appropriate starting materials (where R is other than alkyl, R-iodides or bromides are used) the following compounds can be prepared:
(N-ethyl-3-2',2-difluoroethylbenzylsulfonamido)acetonitrile;
(N-ethyl-3-ethylbenzylsulfonamido)acetonitrile;
(N-ethyl-3-t-butylbenzylsulfonamido)acetonitrile;
(N-ethyl-3-nitrobenzylsulfonamido)acetonitrile;
(N-ethyl-3-ethoxybenzylsulfonamido)acetonitrile;
(N-ethyl-3-2',2',3',3'-tetrafluoropropylbenzylsulfonamido)acetonitrile;
(N-ethyl-2-trifluoromethylbenzylsulfonamido)acetonitrile;
(N-ethyl-2-chlorobenzylsulfonamido)acetonitrile;
(N-ethyl-2,3,6-trichlorobenzylsulfonamido)acetonitrile;
(N-ethyl-2-methoxybenzylsulfonamido)acetonitrile;
(N-ethyl-3-fluorobenzylsulfonamido)acetonitrile;
(N-ethyl-3-bromobenzylsulfonamido)acetonitrile;

(N-ethyl-3-propylbenzylsulfonamido)acetonitrile;
(N-ethyl-3-methoxybenzylsulfonamido)acetonitrile;
(N-ethyl-2,5-di-trifluoromethylbenzylsulfonamido)acetonitrile;
(N-ethyl-3-methyl-5-trifluoromethylbenzylsulfonamido)acetonitrile;
(N-ethyl-3-chloro-4-methoxybenzylsulfonamido)acetonitrile;
(N-ethyl-2-chloro-6-methoxybenzylsulfonamido)acetonitrile;
(N-ethyl-2,3-dichlorobenzylsulfonamido)acetonitrile;
(N-ethyl-2-chloro-4-trifluoromethylbenzylsulfonamido)acetonitrile;
(N-ethyl-2-fluoro-3-chlorobenzylsulfonamido)acetonitrile;
(N-ethyl-3-trifluoromethyl-5-bromobenzylsulfonamido)acetonitrile;
(N-ethyl-2-ethoxy-4-trifluoromethylbenzylsulfonamido)acetonitrile;
(N-ethyl-3-isopropoxybenzylsulfonamido)acetonitrile;
(N-ethyl-3-isopropylbenzylsulfonamido)acetonitrile;
(N-ethyl-2-fluoro-3-chloro-4-trifluoromethylbenzylsulfonamido)acetonitrile;
(N-ethyl-2,3,4-trifluorobenzylsulfonamido)acetonitrile;
(N-ethyl-2,5,6-tribromobenzylsulfonamido)acetonitrile;
(N-ethyl-pentafluorophenylmethylsulfonamido)acetonitrile;
(N-propyl-3-trifluoromethylbenzylsulfonamido)acetonitrile;
(N-butyl-3-2',2'-difluoroethylbenzylsulfonamido)acetonitrile;
(N-pentyl-3-ethylbenzylsulfonamido)acetonitrile;
(N-hexyl-3-ethoxybenzylsulfonamido)acetonitrile;
(N-pentyl-3-fluorobenzylsulfonamido)acetonitrile;
(N-hexyl-3-bromobenzylsulfonamido)acetonitrile;
(N-propyl-3-chloro-4-methoxybenzylsulfonamido)acetonitrile;
(N-cyclopentyl-3-trifluoromethylbenzylsulfonamido)acetonitrile;
(N-2',2'-difluoroethyl-2-chloro-5-trifluoromethylbenzylsulfonamido)acetonitrile;
(N-isopropyl-2-chloro-6-methoxybenzylsulfonamido)acetonitrile;
(N-butyl-3-chloro-4-nitrobenzylsulfonamido)acetonitrile;
(N-hexyl-2-chloro-4-trifluoromethylbenzylsulfonamido)acetonitrile;
(N-pentyl-2-chloro-3-bromobenzylsulfonamido)acetonitrile;
(N-hexyl-2-ethyl-3-trifluoromethylbenzylsulfonamido)acetonitrile;
(N-isopropylthiomethyl-2,5-di-trifluoromethylbenzylsulfonamido)acetonitrile;
(N-propargyl-3-propyl-5-trifluoromethylbenzylsulfonamido)acetonitrile;
(N-hex-4-ynyl-2,6-dichlorobenzylsulfonamido)acetonitrile;
(N-4'-methyl-pent-3-ynyl-4-2',2'-difluoroethyl-3-trifluoromethylbenzylsulfonamido)acetonitrile
(N-3'-iodopropargyl-2-chloro-4-difluoromethylbenzylsulfonamido)acetonitrile;
(N-pen-2-enyl-2,3,5,6-tetrafluorobenzylsulfonamido)acetonitrile;
(N-prop-2-enyl-3-trifluoromethylbenzylsulfonamido)acetonitrile; and
(N-3-methylbut-2-enyl-3-trifluoromethylbenzylsulfonamido)acetonitrile.

(N-methoxymethyl-3-trifluoromethylbenzylsulfonamido)acetonitrile;
(N-1'-methoxyethyl-3-trifluoromethylbenzylsulfonamido)acetonitrile;
(N-3'-propoxypropyl-3-trifluoromethylbenzylsulfonamido)acetonitrile;
(N-2',3'-epoxypropyl-3-trifluoromethylbenzylsulfonamido)acetonitrile;
(N-3',4'-epoxypentyl-3-trifluoromethylbenzylsulfonamido)acetonitrile;
(N-cyclopropylmethyl-3-trifluoromethylbenzylsulfonamido)acetonitrile;
(N-cyclopentyl-3-trifluoromethylbenzylsulfonamido)acetonitrile;
(N-methylthiomethyl-3-trifluoromethylbenzylsulfonamido)acetonitrile;
(N-2'-ethylthiopropyl-3-trifluoromethylbenzylsulfonamido)acetonitrile;
(N-allyl-3-trifluoromethylbenzylsulfonamido)acetonitrile;
(N-hex-4-enyl-3-trifluoromethylbenzylsulfonamido)acetonitrile;
(N-cyclohexyl-3-trifluoromethylbenzylsulfonamido)acetonitrile;
(N-2',2'-dichloroethyl-3-trifluoromethylbenzylsulfonamido)acetonitrile;
(N-2',3'-epoxypropyl-3-ethylbenzylsulfonamido)acetonitrile;
(N-5',6'-epoxyhexyl-3-t-butylbenzylsulfonamido)acetonitrile;
(N-4'-fluorobutyl-3-hexylbenzylsulfonamido)acetonitrile;
(N-2',2'-dichloroethyl-3-ethoxybenzylsulfonamido)acetonitrile;
(N-1'-ethylthiopropyl-3-trifluoromethylbenzylsulfonamido)acetonitrile;
(N-hexylthiomethyl-2-trifluoromethylbenzylsulfonamido)acetonitrile;
(N-isopropylthiomethyl-2-chlorobenzylsulfonamido)acetonitrile;
(N-6'-methylthiohexyl-3-bromobenzylsulfonamido)acetonitrile;
(N-methoxymethyl-2-2',3'-difluoropropylbenzylsulfonamido)acetonitrile;
(N-2'-methoxyethyl-2-chlorobenzylsulfonamido)acetonitrile;
(N-2'-propoxypropyl-3-nitrobenzylsulfonamido)acetonitrile;
(N-2',3'-epoxypropyl-3-iodobenzylsulfonamido)acetonitrile;
(N-3',4'-epoxybutyl-3-bromobenzylsulfonamido)acetonitrile;
(N-3'-iodopropargyl-3-nitrobenzylsulfonamido)acetonitrile;
(N-butyl-3-methoxybenzylsulfonamido)acetonitrile;
(N-pentylthiomethyl-3,5-di-trifluoromethylbenzylsulfonamido)acetonitrile;
(N-2'-propylthiobutyl-2,5-di-trifluoromethylbenzylsulfonamido)acetonitrile;
(N-allyl-2,5-di-trifluoromethylbenzylsulfonamido)acetonitrile;
(N-pent-2-enyl-3,5-di-trifluoromethylbenzylsulfonamido)acetonitrile;
(N-propargyl-3-chloro-4-methoxybenzylsulfonamido)acetonitrile;
(N-ethyl-2'-bromo-3'-fluoropropyl-3-trifluoromethylbenzylsulfonamido)acetonitrile;

(N-4',4'-dichlorobutyl-2-chloro-3-butylbenzylsulfonamido)acetonitrile;
(N-isopropylthiomethyl-2-chloro-4-trifluoromethylbenzylsulfonamido)acetonitrile;
(N-2'-methylthiopropyl-2-fluoro-3-chlorobenzylsulfonamido)acetonitrile;
(N-pentoxymethyl-3-chloro-5-methoxybenzylsulfonamido)acetonitrile;
(N-2',2'-dichloroethyl-2-chloro-3-trifluoromethylbenzylsulfonamido)acetonitrile;
(N-2'-bromo-3'-fluoropropyl-2-bromo-4-trifluoromethylbenzylsulfonamido)acetonitrile;
(N-2'-ethylthioethyl-3-chloro-5-fluorobenzylsulfonamido)acetonitrile;
(N-3'-iodopropargyl-3-trifluoromethylbenzylsulfonamido)acetonitrile;
(N-butyl-3-trifluoromethylbenzylsulfonamido)acetonitrile;
(N-but-2-enyl-3-trifluoromethylbenzylsulfonamido)acetonitrile;
(N-pen-3-enyl-3-trifluoromethylbenzylsulfonamido)acetonitrile;
(N-3'-butoxypropyl-3-trifluoromethylbenzylsulfonamido)acetonitrile; and
(N-isopropoxymethyl-3-difluoromethylbenzylsulfonamido)acetonitrile.

EXAMPLE 3

(N-Methyl-3-Trifluoromethylbenzylsulfonamido)Acetonitrile

In this example 21 ml (0.15 mole) of triethylamine was added over a 5 minute period to a cooled solution containing 16 g (0.15 mole) of the hydrochloride salt of methylaminoacetonitrile in 150 ml of methylene chloride. The mixture was stirred at 20° C. for 15 minutes and then 7.9 g (0.1 mole) of pyridine was added. Then 25.9 g (0.1 mole) of 3-trifluoromethylbenzylsulfonylchloride dissolved in about 50 ml methylene chloride was added to the reaction mixture. The reaction mixture was maintained at 20° C. during the addition and then refluxed for three hours. The mixture was cooled to room temperature and washed once with 200 ml of water and then washed twice with 100 ml of aqueous 5 wt. % hydrochloric acid. The washed mixture was dried over magnesium sulfate and evaporated under vacuum affording 28.2 g of the title compound as a solid residue.

EXAMPLE 4

(N-Cyclopropyl-3-Trifluoromethylbenzylsulfonamido)Acetonitrile (a) In this example 5.3 g of cyclopropylamine were mixed with 9.4 g of triethylamine and then added drop-wise to a solution containing 20 g of 3-trifluoromethylbenzylsulfonyl chloride in methylene chloride at 0° C. The resulting reaction mixture was stirred at room temperature (i.e., about 20°-25° C.) for 3 hours. The reaction mixture was then washed with saturated aqueous ammonium chloride and then with aqueous 1 wt. % hydrochloric acid until it was neutral. The organic layer was then separated, washed twice with 50 ml of aqueous saturated sodium chloride solution, dried over magnesium sulfate and then evaporated to dryness affording 20 g of N-cyclopropyl-3-trifluoromethylbenzylsulfonamide.

(b) 0.26 g of sodium hydride was added portion-wise to a solution containing 2.79 g of N-cyclopropyl-3-trifluoromethylbenzylsulfonamide in 50 ml of dimethylformamide over an ice bath. The mixture was stirred 15 minutes at 01° C. and then 1.26 g of bromoacetonitrile was added drop-wise with cooling. The mixture was stirred overnight at room temperature. Water was then added resulting in the formation of a precipitate and oil. Addition of water was continued until no further precipitate or oil was formed. (About 150 ml of water was used.) The mix was cooled over an ice bath and then filtered. The filter cake was dissolved in hot cyclohexane and then recrystallized affording 0.9 g of the title compound as a solid m.p. 70.1°–71.0° C.

Similarly, by following the same procedure using the corresponding substituted benzylsulfonyl chlorides as starting material, the following compounds can be prepared:
(N-cyclopropyl-3-chlorobenzylsulfonamido)acetonitrile;
(N-cyclopropyl-2-trifluoromethylbenzylsulfonamido)acetonitrile;
(N-cyclopropyl-2-chloro-5-trifluoromethylbenzylsulfonamido)acetonitrile;
(N-cyclopropyl-2,3-dichloro-5-trifluoromethylbenzylsulfonamido)acetonitrile; and
(N-cyclopropyl-pentafluorophenylmethylsulfonamido)acetonitrile.

Similarly by using cyclobutylamine in step 2 the corresponding N-cyclobutyl analogs of the above compounds can be prepared.

EXAMPLE 5

The compounds listed in the following tables were prepared using the general procedures described hereinabove.

TABLE A $$\text{ArCH}_2\text{SO}_2\text{N}(\text{R})\text{—CH}_2\text{CN} \quad (I)$$

| No. | Ar | R | Melting Point °C. |
|---|---|---|---|
| 1 | 3-CF₃φ— | CH₃ | 52–56 |
| 2 | 3-CF₃φ— | CH₃CH₂ | 67–68.5 |
| 3 | 3-CF₃φ— | CH₃(CH₃)₂— | 58–60 |
| 4 | 3-CF₃φ— | CH₃(CH₂)₃— | 66–66.5 |
| 5 | 3-CF₃φ— | CNCH₂— | 150–151 |
| 6 | 2-CF₃φ— | CH₃— | 54–57 |
| 7 | 3-Fφ— | CH₃ | oil |
| 8 | 3-Clφ— | CH₃ | 75–76 |
| 9 | 2-Clφ— | CH₃ | 61–63 |
| 10 | 3-NO₂φ— | CH₃ | 111–112.5 |
| 11 | 3-CH₃φ— | CH₃ | 80–81 |
| 12 | 3-CH₃Oφ— | CH₃ | 79–82 |
| 13 | CH₃COOφ— | CH₃ | 90–93 |
| 14 | 3-Brφ | CH₃ | 98–101 |
| 15 | 3,4-Cl₂φ | CH₃ | 89–91 |
| 16 | 2,4-Cl₂φ | CH₃ | 103–105 |
| 17 | 2,6-Cl₂φCH₃ | | 85–86 |
| 18 | 2,3,4,5,6-F₅φ— | CH₃ | 120–122 |
| 19 | 3-CF₃φ | (CH₃)₂CH— | 96.5–98 |
| 20 | 3-CF₃φ | CH₂=CHCH₂— | 58–59 |
| 21 | 3-CF₃φ | CH₃OCH₂— | 77–78.5 |
| 22 | 3-CF₃φ | CH₃SCH₂— | oil |
| 23I* | 3-CF₃φ | H | 89–91 |
| 24 | 3-CF₃φ | H₂C—O—CHCH₂— (epoxide) | 60–70 |
| 25 | 3,5-Cl₂φ | CH₃ | 95–100 |
| 26 | 2-Cl—5-CF₃φ | CH₃ | 78–84 |
| 27 | 3-CF₃φ | CH₃OCH₂CH₂ | 79–81 |
| 28 | 3-CF₃φ | CF₃CH₂— | 110.5–111.5 |
| 29 | 3-CF₃φ | FCH₂CH₂— | 97.5–100.0 |
| 30 | 3-CF₃φ | ClCH₂CH₂— | 94.5–96.0 |

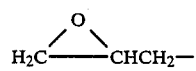

TABLE A-continued $$ArCH_2SO_2N(R)-CH_2CN \quad (I)$$

| No. | Ar | R | Melting Point °C. |
|-----|-----|-----|-----|
| 31 | 3-CF$_3$ø | CH≡C—CH$_2$— | 115–117 |
| 32 | 3-CF$_3$ø | IC≡CCH$_2$— | 99–102 |
| 33 | 3-CF$_3$ø | cyclopropyl | 70.1–71.0 |
| 34 | 3-CF$_3$ø | cyclopropyl-CH$_2$— | 107 |
| 35 | 3-Iø | CH$_3$CH$_2$— | 129–130 |
| 36 | 2-CH$_3$ø | CH$_3$— | 58 |
| 37 | 2-CH$_3$ø | CH$_3$CH$_2$— | 66–67 |
| 38 | 2-CF$_3$ø | CH$_3$CH$_2$— | 67 |
| 39 | 2-Clø | CH$_3$CH$_2$— | 79.5–80.5 |
| 40 | 2,3-Cl$_2$ø | CH$_3$CH$_2$— | 83–85 |
| 41 | 2,5-Cl$_2$ø | CH$_3$— | 104–105 |
| 42 | 2,5-Cl$_2$ø | CH$_3$CH$_2$— | 102 |
| 43 | 3,5-Cl$_2$ø | CH$_3$CH$_2$— | 123–125 |
| 44 | 2-NO$_2$—5-Clø | CH$_3$ | 109–110 |
| 45 | 2-NO$_2$—5-Clø | CH$_3$CH$_2$— | 128–129 |
| 46 | 2-Cl—5-NO$_2$ø | CH$_3$CH$_2$— | 108–110.5 |
| 47 | 3,5-(CF$_3$)$_2$ø— | CH$_3$— | oil |
| 48 | 2-F—5-CF$_3$ø— | CH$_3$CH$_2$— | oil |
| 49 | 2-Cl—5-CF$_3$ø— | CH$_3$CH$_2$— | 108–109 |
| 50 | 2-Br—5-CF$_3$ø— | CH$_3$CH$_2$— | 129–131 |
| 51 | 2,3,6-Cl$_3$ø | CH$_3$ | 88–90 |
| 52 | 2,3,6-Cl$_3$ø | CH$_3$CH$_2$— | 77–80 |
| 53 | 2,3-Cl$_2$—5-CF$_3$ø | CH$_3$ | 104–105 |
| 54 | 2,3-Cl$_2$—5-CF$_3$ø | CH$_3$CH$_2$— | 88.5–89.5 |

*= Phenyl, for example, 2-Clø = 2-chlorophenyl; 3-CF$_3$ø = 3-trifluoromethylphenyl; 3-CH$_3$Oø = 3-methoxyphenyl; 3,4-Cl$_2$ø = 3,4-dichlorophenyl.
*Suffix I designates the compound as an intermediate.

TABLE B

COMPARISON COMPOUNDS $$ArCH_2SO_2N(R)-CH_2CN$$

| No. | Ar | R | Melting Point °C. |
|-----|-----|-----|-----|
| C-1 | 3-CF$_3$ø | CHO | 85–86 |
| C-2 | 3-CF$_3$ø | ø | 72.5–74 |
| C-3 | 3-CF$_3$ø | CH$_3$C(O)— | 135–136 |
| C-4 | 3-CF$_3$ø | ClCH$_2$C(O)— | 120–123 |
| C-5 | 4-CF$_3$ø | CH$_3$ | 78–82 |
| C-6 | 4-Clø | CH$_3$ | 75–77 |
| *C-7 | 3-CNø | CH$_3$ | 72–75 |
| C-8 | 3-CF$_3$ø | øCH(CH$_3$)— | 98–99 |
| C-9 | 3-CF$_3$ø | C$_2$H$_5$OC(O)CH$_2$— | 110–112.5 |
| C-10 | 3-CFø | øCH$_2$—O—CH$_2$— | 44.5–48 |

*C-7 Ar is 3-cyanophenyl

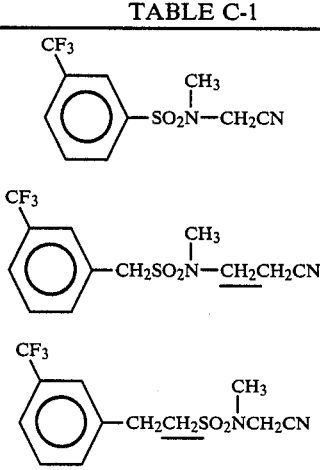

TABLE C-1-continued

| No. | Melting Point °C. |
|-----|-----|
| C-11 | 73–75.5 |
| C-12 | 62–65 |
| C-13 | 44–45 |
| C-14 | oil |

EXAMPLE 6

In this example, the compounds of Example 5 were respectively tested using the procedures described hereinbelow for pre-emergent and post-emergent activity against a variety of grasses and broad-leaf plants including one grain crop and one broad-leaf crop. The compounds tested are identified by compound number in the tables given in Example 5 hereinabove.

PRE-EMERGENT HERBICIDE TEST

Pre-emergence herbicidal activity was determined in the following manner.

Test solutions of the respective compounds were prepared as follows:

355.5 mg of test compound was dissolved in 15 ml of acetone. 2 ml of acetone containing 110 mg of a nonionic surfactant was added to the solution. 12 ml of this stock solution was then added to 47.7 ml of water which contained the same nonionic surfactant at a concentration of 625 mg/l.

Seeds of the test vegetation were planted in a pot of soil and the test solution was sprayed uniformly onto the soil surface at a dose of 27.5 micrograms/cm$^2$ unless otherwise specified in the following Tables. The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests are summarized in Table 1.

POST-EMERGENT HERBICIDAL TEST

The test compound was formulated in the same manner as described above for the pre-emergent test. This formulation was uniformly sprayed on 2 similar pots containing plants 2 to 3 inches tall (except wild oats, soybean and watergrass which were 3 to 4 inches tall) (approximately 15 to 25 plants per pot) at a dose of 27.5 microgram/cm$^2$ unless otherwise specified in the following Tables. After the plants had dried, they were placed in a greenhouse and then watered intermittently at their bases as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity, 100 representing complete kill. The results of these tests are summarized in Table 2.

TABLE 1

Pre-Emergence Herbicidal Activity
Application Rate: 27.5 micrograms/cm$^2$, unless otherwise noted

| | Broad-Leaf Plants % Phytotoxicity | | | | Grasses % Phytotoxicity | | | |
|---|---|---|---|---|---|---|---|---|
| Compound No. | Lambs-quarter | Mus-tard | Pig-weed | Soy-bean | Barnyard-grass | Crab-grass | Wild Oats | Rice |
| 1 | 0 | 0 | 0 | 0 | 98 | 0 | 0 | 0 |
| 2 | 0 | 0 | 0 | 0 | 100 | 0 | 0 | 0 |
| 3 | 0 | 0 | 0 | 0 | 100 | 0 | 0 | 0 |
| 4 | 0 | 0 | 0 | 0 | 95 | 0 | 0 | 0 |
| 5 | 0 | 0 | 0 | 0 | 99 | 0 | 0 | 0 |
| 6 | 0 | 0 | 0 | 0 | 100 | 0 | 0 | 0 |
| 7 | 0 | 0 | 0 | 0 | 65 | 0 | 0 | 40 |
| 8 | 0 | 0 | 0 | 0 | 100 | 0 | 0 | 0 |
| 9 | 0 | 0 | 0 | 0 | 90 | 0 | 0 | 0 |
| 10 | 0 | 35 | 0 | 15 | 92 | 0 | 0 | 0 |
| 11 | 0 | 0 | 0 | 0 | 100 | 0 | 0 | 0 |
| 12 | 0 | 0 | 0 | 0 | 85 | 0 | 0 | 0 |
| 13 | 0 | 0 | 0 | 0 | 85 | 0 | 0 | 0 |
| 14 | 0 | 0 | 0 | 0 | 100 | 0 | 0 | 0 |
| 15 | 0 | 0 | 0 | 0 | 100 | 0 | 0 | 0 |
| 16 | 0 | 0 | 0 | 0 | 97 | 0 | 0 | 0 |
| 17 | 0 | 0 | 0 | 0 | 94 | 0 | 0 | 0 |
| 18 | 0 | 0 | 0 | 0 | 100 | 0 | 0 | 0 |
| 19 | 0 | 0 | 0 | 0 | 85 | 0 | 0 | 0 |
| 20 | 0 | 0 | 0 | 0 | 100 | 0 | 0 | 0 |
| 21 | 0 | 0 | 0 | 0 | 100 | 0 | 0 | 0 |
| 22 | 0 | 0 | 0 | 0 | 100 | 0 | 0 | 0 |
| 23I | 0 | 0 | 0 | 0 | 0 | 0 | 0 | 0 |
| 24 | 0 | 0 | 0 | 0 | 80 | 0 | 0 | 0 |
| 25 | 0 | 0 | 0 | 0 | 100 | 0 | 0 | 0 |
| 26 | 0 | 0 | 0 | 5 | 99 | 0 | 0 | 0 |
| 27 | 0 | 0 | 0 | 0 | 93 | 0 | 0 | 0 |
| 28 | 0 | 0 | 0 | 0 | 100 | 0 | 0 | 0 |
| 29 | 0 | 0 | 0 | 0 | 100 | 0 | 0 | 0 |
| 30 | 0 | 0 | 0 | 0 | 100 | 0 | 0 | 0 |
| 31 | 0 | 0 | 0 | 0 | 100 | 0 | 0 | 0 |
| 32 | 0 | 0 | 0 | 0 | 100 | 0 | 0 | 0 |
| 33 | 0 | 0 | 0 | 0 | 100 | 0 | 0 | 0 |
| 34 | 0 | 0 | 0 | 0 | 100 | 0 | 0 | 0 |
| 35 | 0 | 0 | 0 | 0 | 100 | 0 | 0 | 0 |
| 36 | 0 | 0 | 0 | 0 | 90 | 0 | 0 | 0 |
| 37 | 0 | 0 | 0 | 0 | 100 | 0 | 0 | 0 |
| 38 | 0 | 0 | 0 | 0 | 100 | 0 | 0 | 0 |
| 39 | 0 | 0 | 0 | 5 | 100 | 0 | 0 | 0 |
| 40 | 0 | 0 | 0 | 0 | 100 | 0 | 0 | 0 |
| 41 | 0 | 0 | 0 | 0 | 100 | 0 | 0 | 0 |
| 42 | 0 | 0 | 0 | 0 | 100 | 0 | 0 | 0 |
| 43 | 0 | 0 | 0 | 0 | 90 | 0 | 0 | 0 |
| 44 | 0 | 0 | 0 | 0 | 100 | 0 | 0 | 0 |
| 45 | 0 | 0 | 0 | 0 | 100 | 0 | 0 | 0 |
| 46 | 0 | 0 | 0 | 0 | 100 | 0 | 0 | 0 |
| 47 | 0 | 0 | 0 | 0 | 100 | 0 | 0 | 0 |
| 48 | 0 | 0 | 0 | 0 | 100 | 0 | 0 | 0 |
| 49 | 95 | 100 | 100 | 0 | 100 | 30 | 0 | 0 |
| 50 | 0 | 0 | 0 | 0 | 100 | 0 | 0 | 0 |
| 51 | 0 | 0 | 0 | 20 | 95 | 0 | 0 | 0 |
| 52 | 0 | 0 | 0 | 0 | 100 | 0 | 0 | 0 |
| 53 | 30 | 0 | 80 | 0 | 100 | 0 | 0 | 0 |
| 54 | 90 | 0 | 85 | 0 | 100 | 20 | 0 | 0 |

TABLE 1A

COMPARISON COMPOUNDS
Pre-Emergence Herbicidal Activity
Application Rate: 27.5 micrograms/cm$^2$, unless otherwise noted

| | Broad-Leaf Plants % Phytotoxicity | | | | Grasses % Phytotoxicity | | | |
|---|---|---|---|---|---|---|---|---|
| Compound No. | Lambs-quarter | Mus-tard | Pig-weed | Soy-bean | Barnyard-Grass | Crab-grass | Wild Oats | Rice |
| C-1 | 0 | 0 | 0 | 0 | 0 | 0 | 0 | 0 |
| C-2 | 0 | 0 | 0 | 0 | 0 | 0 | 0 | 0 |
| C-3 | 0 | 0 | 0 | 0 | 0 | 0 | 0 | 0 |
| C-4 | 0 | 0 | 0 | 0 | 0 | 0 | 0 | 0 |
| C-5 | 0 | 0 | 0 | 0 | 0 | 0 | 0 | 0 |
| C-6 | 0 | 0 | 0 | 0 | 25 | 0 | 0 | 0 |
| C-7 | 0 | 0 | — | 0 | 0 | 0 | 0 | 0 |
| C-8 | 0 | 0 | — | 0 | 0 | 0 | 0 | 0 |
| C-9 | 0 | 0 | 0 | 0 | 0 | 0 | 0 | 0 |

TABLE 1A-continued

COMPARISON COMPOUNDS
Pre-Emergence Herbicidal Activity
Application Rate: 27.5 micrograms/cm$^2$, unless otherwise noted

| Compound No. | Broad-Leaf Plants % Phytotoxicity | | | | Grasses % Phytotoxicity | | | |
|---|---|---|---|---|---|---|---|---|
| | Lambs-quarter | Mus-tard | Pig-weed | Soy-bean | Barnyard-Grass | Crab-grass | Wild Oats | Rice |
| C-10 | 0 | 0 | 0 | 0 | 0 | 0 | 0 | 0 |
| C-11 | 0 | 0 | 0 | 0 | 0 | 0 | 0 | 0 |
| C-12 | 80 | 0 | 0 | 40 | 0 | 0 | 0 | 0 |
| C-13 | 0 | 0 | 65 | 15 | 0 | 0 | 0 | 0 |
| C-14 | 0 | 0 | 0 | 0 | 45 | 0 | 0 | 0 |

TABLE 2

Post-Emergence Herbicidal Activity
Application Rate: 27.5 micrograms/cm$^2$, unless otherwise noted

| Compound No. | Broad-Leaf Plants % Phytotoxicity | | | | Grasses % Phytotoxicity | | | |
|---|---|---|---|---|---|---|---|---|
| | Lambs-quarter | Mus-tard | Pig-weed | Soy-bean | Barnyard-grass | Crab-grass | Wild Oats | Rice |
| 1 | 0 | 0 | 0 | 10 | 100 | 0 | 15 | 0 |
| 2 | 0 | 0 | 0 | 0 | 100 | 0 | 0 | 0 |
| 3 | 0 | 0 | 0 | 0 | 100 | 0 | 0 | 0 |
| 4 | 0 | 0 | 0 | 0 | 95 | 0 | 0 | 0 |
| 5 | 0 | 0 | 0 | 0 | 88 | 0 | 0 | 0 |
| 6 | 0 | 0 | 0 | 0 | 100 | 0 | 0 | 0 |
| 7 | 0 | 0 | 0 | 0 | 97 | 0 | 0 | 0 |
| 8 | 0 | 0 | 0 | 0 | 100 | 0 | 0 | 0 |
| 9 | 0 | 0 | 0 | 0 | 73 | 0 | 0 | 0 |
| 10 | 0 | 0 | 0 | 0 | 45 | 0 | 0 | 0 |
| 11 | 0 | 0 | 0 | 0 | 100 | 0 | 0 | 0 |
| 12 | 0 | 0 | 0 | 0 | 83 | 0 | 0 | 0 |
| 13 | 0 | 0 | 0 | 0 | 20 | 0 | 0 | 0 |
| 14 | 0 | 0 | 0 | 0 | 50 | 0 | 0 | 0 |
| 15 | 0 | 0 | 0 | 0 | 95 | 0 | 0 | 0 |
| 16 | 0 | 0 | 0 | 0 | 65 | 0 | 0 | 0 |
| 17 | 0 | 0 | 0 | | 80 | 0 | | 0 |
| 18 | 0 | 0 | 0 | 0 | 100 | 0 | 0 | 0 |
| 19 | 0 | 0 | 0 | 0 | 70 | 0 | 0 | 0 |
| 20 | 0 | 0 | 0 | 0 | 100 | 0 | 0 | 0 |
| 21 | 0 | 0 | 0 | 0 | 0 | 0 | 0 | 0 |
| 22 | 0 | 0 | 0 | 0 | 80 | 0 | 0 | 0 |
| 23I | 0 | 0 | 0 | 0 | 0 | 0 | 0 | 0 |
| 24 | 0 | 0 | 0 | 0 | 100 | 0 | 0 | 0 |
| 25 | 0 | 0 | 0 | 0 | 100 | 0 | 0 | 0 |
| 26 | 0 | 0 | 0 | 30 | 100 | 0 | 0 | 0 |
| 27 | 0 | 0 | 0 | 0 | 99 | 0 | 0 | 0 |
| 28 | 0 | 0 | 0 | 0 | 90 | 0 | 0 | 0 |
| 29 | 0 | 0 | 0 | 0 | 100 | 0 | 0 | 0 |
| 30 | 0 | 0 | 0 | 0 | 98 | 0 | 0 | 0 |
| 31 | 0 | 0 | 0 | 0 | * | 0 | 0 | 0 |
| 32 | 0 | 0 | 0 | 0 | 100 | 0 | 0 | 0 |
| 33 | 0 | 0 | 0 | 0 | 100 | 0 | 0 | 0 |
| 34 | 0 | 0 | 0 | 0 | 100 | 0 | 0 | 0 |
| 35 | 0 | 0 | 0 | 0 | 100 | 0 | 0 | 0 |
| 36 | 0 | 0 | 0 | 0 | 100 | 0 | 0 | 0 |
| 37 | 0 | 0 | 0 | 0 | 100 | 0 | 0 | 0 |
| 38 | 0 | 0 | 0 | 0 | 100 | 0 | 0 | 0 |
| 39 | 0 | 0 | 0 | 0 | 100 | 0 | 0 | 0 |
| 40 | 0 | 0 | 0 | 0 | 100 | 0 | 0 | 0 |
| 41 | 0 | 0 | 0 | 0 | 100 | 0 | 0 | 0 |
| 42 | 0 | 0 | 0 | 0 | 100 | 0 | 0 | 0 |
| 43 | 0 | 20 | 20 | 20 | 100 | 0 | 0 | 0 |
| 44 | 0 | 0 | 0 | 0 | 100 | 0 | 0 | 0 |
| 45 | 0 | 0 | 0 | 0 | 98 | 0 | 0 | 0 |
| 46 | 0 | 0 | 0 | 0 | 100 | 0 | 0 | 0 |
| 47 | 0 | 0 | 0 | 0 | 98 | 0 | 0 | 0 |
| 48 | 0 | 0 | 0 | 0 | 100 | 0 | 0 | 0 |
| 49 | 10 | 30 | 10 | 30 | 100 | 0 | 0 | 0 |
| 50 | 0 | 0 | 0 | 0 | 100 | 0 | 0 | 0 |
| 51 | 0 | 0 | 0 | 0 | * | 0 | 0 | 0 |
| 52 | 0 | 0 | 0 | 0 | 100 | 0 | 0 | 0 |
| 53 | * | 0 | 0 | 0 | 100 | 0 | 0 | 0 |
| 54 | 0 | 0 | 0 | 0 | 100 | 0 | 0 | 0 |

*Not tested at this rate.

TABLE 2A

COMPARISON COMPOUNDS
Post-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambs-quarter | Mus-tard | Pig-weed | Soy-bean | Barnyard-grass | Crab-grass | Wild Oats | Rice |
| C-1 | 0 | 0 | 0 | 10 | 0 | 0 | 0 | 0 |
| C-2 | 0 | 0 | 0 | 0 | 0 | 0 | 0 | 0 |
| C-3 | 0 | 0 | 0 | 0 | 0 | 0 | 0 | 0 |
| C-4 | 0 | 0 | 0 | 0 | 0 | 0 | 0 | 0 |
| C-5 | 0 | 0 | 0 | 0 | 0 | 0 | 0 | 0 |
| C-6 | 0 | 0 | 0 | 0 | 10 | 0 | 0 | 0 |
| C-7 | 0 | 0 | 0 | 0 | 0 | 0 | 0 | 0 |
| C-8 | 0 | 0 | 0 | 0 | 0 | 0 | 0 | 0 |
| C-9 | 0 | 0 | 0 | 0 | 0 | 0 | 0 | 0 |
| C-10 | 0 | 0 | 0 | 0 | 0 | 0 | 0 | 0 |
| C-11 | 0 | 0 | 0 | 0 | 0 | 0 | 0 | 0 |
| C-12 | 0 | 0 | 0 | 0 | 0 | 0 | 0 | 0 |
| C-13 | 0 | 20 | 30 | 35 | 0 | 0 | 0 | 0 |
| C-14 | 0 | 0 | 0 | 15 | 0 | 0 | 0 | 0 |

As can be seen from the above Tables, the compounds of the invention generally exhibited good to excellent selective phytotoxicity against barnyardgrass and especially so Compounds Nos. 1, 2, 8, 18. In each case the compounds did not exhibit any post-emergence phytotoxicity with respect to rice and in only one instance exhibited any significant pre-emergence phytotoxicity with respect to rice. Moreover, from the comparison compounds it can be seen that even closely related compounds do not possess the excellent selective phytotoxicity against barnyardgrass shown by Applicant's compounds.

Obviously, many modifications and variations of the invention described hereinabove and below can be made without departing from the essence and scope thereof.

What is claimed is:

1. A compound having the formula:

R is lower alkyl having 1 through 6 carbon atoms; cycloalkyl having 3 through 6 carbon atoms; cycloalkylalkyl wherein the cycloalkyl moeity has 3 through 6 carbon atoms and the alkyl moiety has 1 or 2 carbon atoms; lower alkenyl having 2 through 6 carbon atoms; lower alkynyl having 2 through 6 carbon atoms; 3-iodopropargyl; alkoxyalkyl wherein the alkoxy and alkyl moeities independently have 1 through 6 carbon atoms; alkylthioalkyl wherein the alkyl moieties thereof independently have 1 through 6 carbon atoms; epoxyalkylmethylene having 2 through 6 carbon atoms; haloalkylmethyl having 2 through 4 carbon atoms and 1 through 4 halo atoms independently selected from the group of fluoro, chloro and bromo; or cyanomethyl; and Ar is substituted phenyl selected from the group of tetrafluorophenyl; pentafluorophenyl; trisubstituted phenyls having three substitutents independently selected from the group of fluoro, chloro, bromo and trifluoromethyl; and substituted phenyls having the formulas

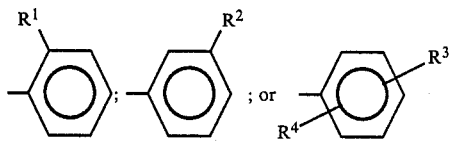

wherein $R^1$ is methyl, trifluoromethyl or chloro;
$R^2$ is halo, alkyl having 1 through 4 carbon atoms, alkoxy having 1 through 4 carbon atoms, fluoroalkyl having 1 through 4 fluoro atoms and 1 through 4 carbon atoms or nitro; one of $R^3$ or $R^4$ is trifluoromethyl or chloro and the other is halo, nitro, alkyl having 1 through 4 carbon atoms, alkoxy having 1 through 4 carbon atoms, or fluoroalkyl having 1 through 4 fluoro atoms and 1 through 4 carbon atoms.

2. The compound of claim 1 wherein R is alkyl having 1 through 4 carbon atoms; cyclopropyl; cyclopropylmethyl; alkenyl having 2 through 4 carbon atoms; lower alkynyl having 3 or 4 carbon atoms; 3-iodopropargyl; alkoxyalkyl wherein the alkoxy and alkyl moieties independently have 1 through 4 carbon atoms; alkylthioalkyl wherein the alkyl moieties independently having 1 through 4 carbon atoms; epoxyalkylmethylene having 2 through 6 carbon atoms; haloalkylmethyl having 2 through 4 carbon atoms and 1 through 4 halo atoms independently selected from the group of fluoro, chloro and bromo, or cyanomethyl; and Ar is selected from the group of tetrafluorophenyl; pentafluorophenyl; trisubstituted phenyl having three substituents independently selected from the group of chloro, bromo, and trifluoromethyl; and substituted phenyls having the formulas

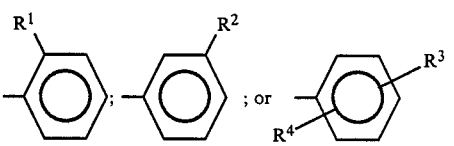

wherein $R^1$ is trifluoromethyl or chloro;
$R^2$ is halo or trifluoromethyl; and
one of $R^4$ or $R^5$ is trifluoromethyl or halo.

3. The compound of claim 1, having the formula

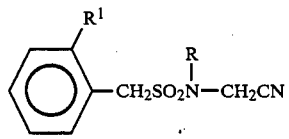

wherein R and $R^1$ are as defined in claim 1.

4. The compound of claim 3 wherein R is methyl, ethyl, propyl, cyclopropyl, allyl, propargyl, 3-iodopropargyl; methoxymethyl, 2-fluoroethyl, or 2,2,2-trifluoroethyl.

5. The compound of claim 3 wherein R is methyl, ethyl, propargyl, 3-iodopropargyl, 2-fluoroethyl, or 2,2,2-trifluoroethyl.

6. The compound of claim 3 wherein $R^1$ is trifluoromethyl, or chloro.

7. The compound of claim 6 wherein $R^1$ is trifluoromethyl.

8. The compound of claim 4 wherein $R^1$ is trifluoromethyl.

9. The compound of claim 5 wherein $R^1$ is trifluoromethyl.

10. The compound of claim 1 having the formula

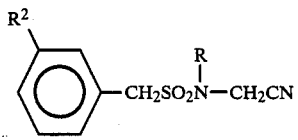

wherein R and $R^2$ are as defined in claim 1.

11. The compound of claim 10 wherein R is methyl, ethyl, propyl, cyclopropyl, allyl, propargyl, 3-iodopropargyl, methoxymethyl, 2-fluoroethyl, or 2,2,2-trifluoroethyl.

12. The compound of claim 11 wherein R is methyl, ethyl, propargyl, 3-iodopropargyl, 2-fluoroethyl, or 2,2,2-trifluoroethyl.

13. The compound of claim 10 wherein $R^2$ is trifluoromethyl, or chloro.

14. The compound of claim 11 wherein $R^2$ is trifluoromethyl.

15. The compound of claim 12 wherein $R^2$ is trifluoromethyl.

16. The compound of claim 15 wherein R is ethyl.

17. The compound of claim 11 wherein $R^2$ is chloro.

18. The compound of claim 12 wherein $R^2$ is chloro.

19. The compound of claim 18 wherein R is ethyl.

20. The compound of claim 1 having the formula

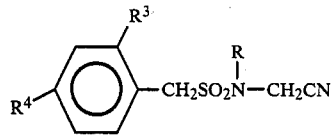

wherein R, $R^3$ and $R^4$ are as defined in claim 1.

21. The compound of claim 20 wherein R is methyl, ethyl, propyl, cyclopropyl, allyl, propargyl, 3-iodopropargyl, methoxymethyl, 2-fluoroethyl, or 2,2,2-trifluoroethyl.

22. The compound of claim 20 wherein R is methyl, ethyl, propargyl, 3-iodopropargyl, methoxymethyl, 2-fluoroethyl, or 2,2,2-trifluoroethyl.

23. The compound of claim 20 wherein one of $R^3$ is $R^4$ is trifluoromethyl or chloro and the other is trifluoromethyl or halo.

24. The compound of claim 20 wherein $R^3$ and $R^4$ are each chloro.

25. The compound of claim 24 wherein R is methyl or ethyl.

26. The compound of claim 1 wherein Ar is a trisubstituted phenyl having three substituents independently selected from the group of fluoro, chloro, bromo, and trifluoromethyl.

27. The compound of claim 26 wherein R is methyl ethyl, propargyl, 3-iodopropargyl, methoxymethyl, 2-fluoroethyl, or 2,2,2-trifluoroethyl.

28. The compound of claim 26 wherein said trisubstituted phenyl substituents are independently selected from the group of trifluoromethyl and chloro.

29. The compound of claim 28 wherein R is ethyl and Ar is 2,3,-dichloro-5-trifluoromethylphenyl.

30. The compound of claim 1 wherein Ar is pentafluoromethyl.

31. The compound of claim 1 wherein Ar is 2-chloro-5-trifluoromethylphenyl and R is methyl.

32. The compound of claim 1 wherein Ar is 2-chloro-5trifluoromethylphenyl and R is ethyl.

33. The compound of claim 1 wherein Ar is 3,5-dichlorophenyl and R is methyl.

34. The compound of claim 1 wherein Ar is 3,5-dichlorophenyl and R is ethyl.

35. The compound of claim 1 wherein Ar is tetrafluorophenyl.

* * * * *